Figure 1:
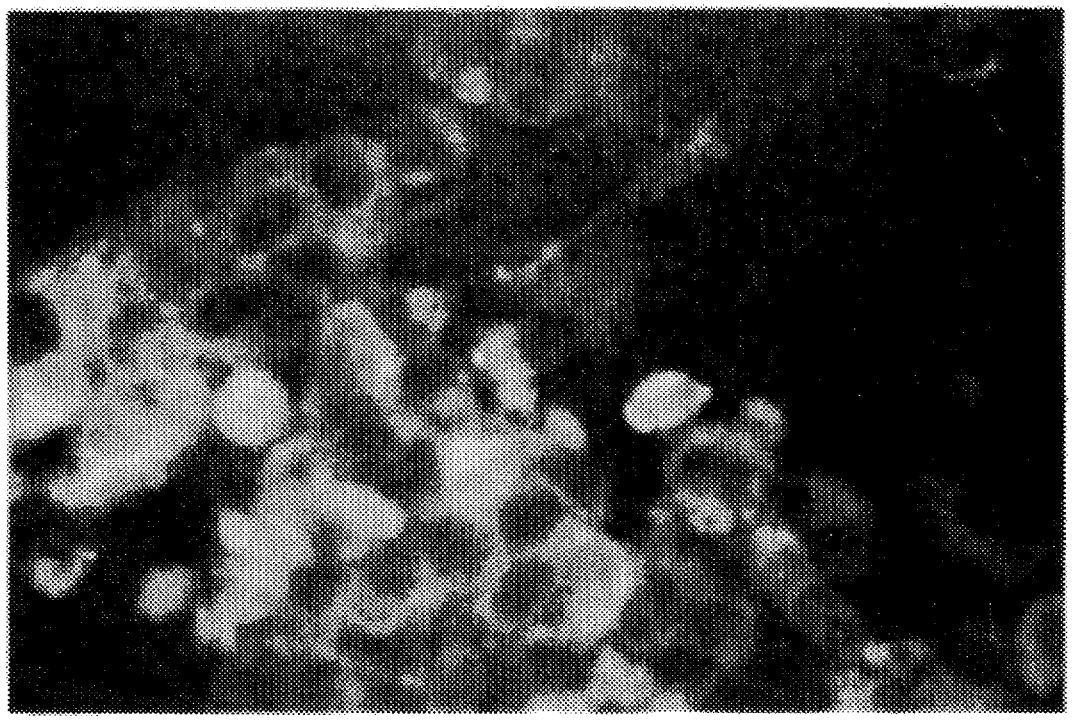

United States Patent [19]
Brentani et al.

[11] Patent Number: 5,679,530
[45] Date of Patent: Oct. 21, 1997

[54] ISOLATED PROTEIN HAVING MOLECULAR WEIGHT OF FROM ABOUT 55 KILODALTONS TO ABOUT 65 KILODALTONS (SDS-PAGE) WHICH BINDS TO PRION PROTEIN

[75] Inventors: Ricardo Renzo Brentani; Sandro Jose de Souza, both of Sao Paulo, Brazil

[73] Assignee: Ludwig Institute for Cancer Research, New York, N.Y.

[21] Appl. No.: 421,059

[22] Filed: Apr. 12, 1995

[51] Int. Cl.$^6$ .................. G01N 33/567; G01N 33/566; G01N 33/569; C07K 7/08; C07K 14/705; A61K 38/10; A61K 39/00

[52] U.S. Cl. .................. 435/7.1; 424/185.1; 424/186.1; 424/204.1; 530/326; 530/350; 530/826

[58] Field of Search .................... 530/350, 826; 435/7.1; 424/204.1, 185.1, 186.1

[56] References Cited

PUBLICATIONS

Sigma Chemical Catalog, see p. 1598 1993.
Tagliavani et al. PNAS 90:9678–9682 Oct. 1993.
Forloni et al. PNAS 362:543–546 Apr. 1993.
Ghiso et al. PNAS 87:1288–1291 Feb. 1990.
Elton et al. PNAS 85:2518–2522 Apr. 1988.
Lazar et al. Mol. Cell. Biology 8(3):1247–1252 1988.
Burgess et al. J. Cell Biology 111:2129–37 1990.
Brentani, "Biological Implications of Complementary Hydropathy of Amino Acids," J. Theor. Biol., 133: 495–499 (1988).
Brentani, "Complementary Hydropathy and the Evolution of Interactive Polypeptides," J. Mol. Evol. 31: 239–243 (1990).
Goldgaber, "Anticipating The Anti–Prion Protein," Nature 351: (May 9, 1991).
Manson, et al., "Anti–prions and other agents," Nature 352: (Jul. 25, 1991).
Hewinson, et al., "Anti–prions and other agents," Nature 352: (Jul. 25, 1991).
Bendheim, et al., "Anti–prions and other agents," Nature 352: 291–292 (Jul. 25, 1991).
Moser, et al., "An anti–prion protein?", Nature 362: 213–214 (Mar. 18, 1993).

Primary Examiner—Anthony C. Caputa
Attorney, Agent, or Firm—Felfe & Lynch

[57] ABSTRACT

The invention involves an isolated anti prion protein binding protein which has a molecular weight of from about 55 kD to about 65 kD as determined by SDS-PAGE. Also described is a peptide derived from this isolated anti-prion protein binding protein. Diagnostic uses for each of these molecules are discussed.

8 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 17 amino acid residues
        ( B ) TYPE: amino acid
        ( D ) TOPOLOGY: linear ( i i ) MOLECULE TYPE: protein ( x i ) SEQUENCE DESCRIPTION: SEQ ID NO: 1:

Tyr His Val Ala Thr Lys Ala Pro His His Gly Pro Cys Arg Ser Ser
              5                      10                  15
Ala

ISOLATED PROTEIN HAVING MOLECULAR WEIGHT OF FROM ABOUT 55 KILODALTONS TO ABOUT 65 KILODALTONS (SDS-PAGE) WHICH BINDS TO PRION PROTEIN

FIELD OF THE INVENTION

This invention relates to the isolation of a protein which binds with prion protein, referred to hereafter as PrP. More particularly, the isolated protein of the invention has a molecular weight of from about 55 kD to about 65 kD as determined by SDS-PAGE, and is referred to hereafter as anti-PrP protein or PrP binding protein. Also described is an isolated peptide consisting of an amino acid sequence from said binding protein/antiPrP protein. Both the peptide and the protein have various diagnostic efficacies. In the case of the peptide, it can be used, e.g., to produce antibodies which are in turn used to identify the anti-PrP protein. Also, the peptide can bind, itself, to PrP. Similarly, the full protein may be used in the same way. Various diseases associated with prions can thus be diagnosed or screened using these materials. Further, one can screen for the presence of PrP in a sample using the protein of the invention.

BACKGROUND AND PRIOR ART

"Prions" or "protein infectious particles", have been implicated in a number of pathological conditions. Known prion associated diseases are referred to generally as spongiform encephalopathies, due to a common feature of the diseases, i.e., the formation of "holes" in cranial tissue.

By far the most commonly recognized disease associated with prions is "scrapie", found in sheeps and goats. Afflicted animals lose coordination, and eventually become unable to stand. Additional animal disorders associated with prions include transmissible mink encephalopathy; chronic wasting disease of mule, deer and elk; feline spongiform encephalopathy; and bovine spongiform encephalopathy ("mad cow disease"). Among humans, Kuru, or "laughing death" has been associated with cannibalism. By far the most serious human disorder associated with prions, however, is Creutzfeldt-Jakob disease. This condition generally becomes evident via the development of dementia in the subject. It is a cause of great concern because it can be transmitted iatrogenically, such as by corneal transplantation, use of contaminated surgical instruments, injection of purified growth hormones or other pituitary based materials, as well as via implantation of dura mater or electrodes in the brain. Additional pathological conditions associated with prions include Gerstmann-Sträussler-Scheinker disease (lataxia and cerebellum damage), and fatal familial insomnia. Both of these conditions are inheritable, and typically appear in midlife.

At first, the aforementioned conditions were believed to be caused by a slow acting virus found in cerebral tissue. This hypothesis was based upon the observation that the diseases could be transmitted by injection of brain extracts of afflicted animals into healthy animals. This hypothesis, however, is generally no longer accepted, because a virus has not been isolated in spite of concerted efforts to do so.

What has been found about these conditions is that, although inheritable, they are caused by proteinaceous material, rather than by nucleic acids. The proteinaceous material is referred to as the prion. Among the experiments which led to the hypothesis that protein material was implicated was the treatment of materials from infected animals to inactivate proteins but not nucleic acids. Under these conditions, the disease was not transmitted.

Elaborations on this hypothesis have identified a single protein in scrapie prions. This protein, "prion protein", will be referred to as—PrP—hereafter. It is used, generically, to refer to the protein which forms the prion. See, e.g., Prusener, Science 252:1512–1522 (Jun. 14, 1991) ("Molecular Biology of Prion Diseases"); Prusiner, et al, ed., Prion Diseases of Humans And Animals (Ellis Horwood, 1992).

As with all proteins, PrP is encoded by a gene; however, expression of PrP is not sufficient to cause a prion associated condition. It has been determined that PrP may undergo changes in its three dimensional structure, leading to its prion form. To elaborate, the benign from of PrP shows a multiple alpha helix geometry. In the form of prions, however, the three dimensional structure "elongates", forming beta sheets. In summary, the difference between the normal, harmless form of PrP and the form associated with diseases, e.g., appears to be completely conformational.

"Complementary hydropathy", a concept critical to understanding the invention described herein, was first suggested by Biro, Medical Hypothesis 7:981 (1981). The concept Biro set forth was based upon an observation that protein/protein interactions were observed to be specific. He argued that complementary coding, i.e., coding by both sense and "anti-sense" strands of nucleic acid molecules could lead to the required specificity. Work on the interaction between ACTH, λ-endorphin, angiotensin II, luteinizing hormone release hormone, and fibronectin, and their receptors, supports this hypothesis. See Bost, et al, Mol. Cell Endocrin 44:1 (1986) (ACTH); Carr, et al, J. Neuroimmunol 12:329 (1986) (λ-endorphin), Elton, et al, Proc. Natl. Acad. Sci. USA 85:2518 (1988); (angiotensin II); Mulchahey, et al, Proc. Natl. Acad. Sci. USA 83: 9714 (1986) (luteinizing hormone-releasing hormone); and Brentani, et al, Proc. Natl. Acad. Sci. USA 85:364 (1988) (fibronectin).

All of this work supported a concept hypothesized by Blalock, et al, Biochem. Biophys. Res. Commun. 121: 203 (1984). Their observation was that when the codons for hydropathic amino acids were compared to their complementary codons, these complementary codons were generally codons which code hydrophilic amino acids. Blalock, et al observed a significant correlation (r=0.74) between hydropathic coefficients of amino acids encoded for by opposing DNA strands, and thus postulated that peptides encoded by complementary DNA strands would bind one another. As indicated, supra, this hypothesis is supported for a number of peptides.

In 1991, Goldgaber, Nature 351:106 (May 9, 1991), reported on the possible application of complementarity to PrP. Goldgaber reported analyzing PrP complementary DNA sequences, and the identification of a large, overlapping open reading frame in the DNA "antisense" strand for the PrP gene. When Goldgaber analyzed the deduced amino acid sequence for this complementary coding region, he found it to be nearly a mirror image of PrP. Goldgaber is incorporated by reference in its entirety. While Manson, et al, Nature 352: 291 (Jul. 25, 1991), questioned this work, Hewinson, et al, Nature 352:291 (Jul. 25, 1991) noted that it confirmed their own work. Prusiner, et al, Nature 362: 213 (Mar. 18, 1993), provided an interesting "wrinkle" on this research, when they reported that they did find an RNA unit of the proper size (4.5 kb) for hybridizing to PrP sense strands, but it was not derived from the antisense PrP strand.

The reports discussed supra, as well as a report by Moser, et al, Nature 362:213 (Mar. 18, 1993), discuss the possibility of the anti-PrP protein, as it will be referred to hereafter, in prion associated diseases. Hewinson, et al suggested that the complementary protein might be a PrP receptor.

Figure 2:
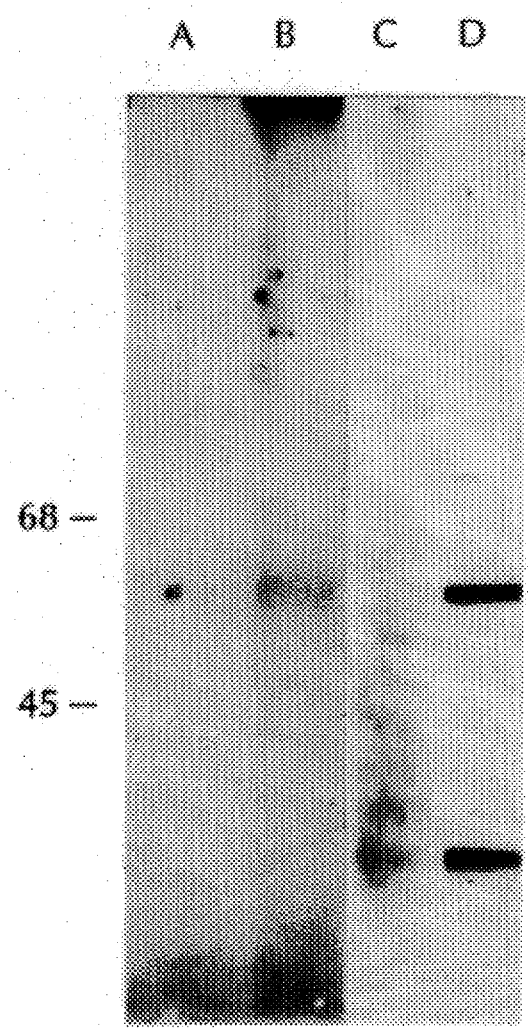

The work which follows presents, for the first time, the identification and characterization of an anti-PrP binding protein. This material may be used to identify the presence of PrP in samples, thus providing a method of screening and/or diagnosis, especially when other symptoms characteristic of a prion associated disorder are observed. In view of the prelevance of prion associated disorders in livestock, e.g., there are both human and veterinary uses for the invention.

BRIEF DESCRIPTION OF THE FIGURE

FIG. 1 shows the results of an immunofluorescence assay, using antibodies produced with the peptide of the invention.

FIG. 2 depicts analyses on SDS-PAGE. In lane A, eluates from cells which were negative in the immunofluorescence assay are presented. Lane B was obtained using eluates from positive cells. Lane C is a Western blot of an eluate of lane B, using normal mouse serum, while lane D resulted from testing such an eluate with the antiserum obtained using the peptide of the invention.

DETAILED DESCRIPTION OF PREFERRED EMBODIMENTS

EXAMPLE 1

In order to approach the question of whether an anti-prion protein exists, a peptide was synthesized, based upon the work of Forloni, et al, Nature 362:543–546 (1993), the disclosure of which is incorporated by reference in its entirety. Forloni et al disclose prion peptide "PrP 106–126", which induced cell death in primary rat hippocampal cultures. The peptide, which was used herein, i.e.:

Tyr His Val Ala Thr Lys Ala Pro His His Gly Pro Cys Arg Ser Ser Ala (SEQ ID NO: 1) is complementary to a peptide derived from PrP, and is itself derived from complementary amino acids 106–126 of a deduced anti-prion ORF, supra.

The synthesized peptide was coupled to Keyhole limpet hemocyanin (KLH), to produce an immunogen. The immunogen was then injected into mice, intraperitoneally, at two week intervals, to a total of 100 ug of total protein. After the fourth injection, animals were bled, and titered against uncoupled peptide, via a standard ELISA.

EXAMPLE 2

Once the antiserum was made, it was utilized in immunofluorescence studies. Murine neuroblastoma cell line "neuro 2A" was used. Samples of the cell line were plated ($2\times10^6$ cells/well), in eight well tissue culture chamber slides. The cells were incubated, overnight, after which the slides were washed and the cells fixed with 1% glutaraldehyde. After fixing, a 1:20 horse serum solution was added, for 1 hour at 37° C. A wash with phosphate buffered saline (PBS) followed, and then the antiserum was added, for a period of 2 hours. Following this, the cells were washed extensively, after which a second antibody, i.e., anti-IgG, coupled to fluorescein isothiocyanate, diluted 1:80 in Evan's blue, was added, for 1 hour. Extensive washing followed, after which the slides were mounted, and observed.

FIG. 1 shows these results, although black and white reproduction does not show very clearly the fact that FITC labelling did in fact take place (a green color shows that the labelling did take place). The results do show that the antiserum recognized the surface of the neuro 2A cells. The total reactivity was about 15% of the total population. This result is analogous to results obtained by Butler, et al, J. Virol 62: 1558–1564 (1988), who showed that $Prp^{sc}$ infectability in neuro 2A cells was restricted to only certain cells in the population. The observation reported herein suggested the next set of experiments, designed to analyze any possible differences between negative and positive cells.

EXAMPLE 3

In these experiments, positive and negative cells were first cloned by limiting dilution. The positive cells derived from clone "IEI2" and the negative cells from clone "IC4".

Living cells of each clone were surface labelled with $^{125}I$, using the well known lactoperoxidase method. Following labelling, the cells were lysed, and the resulting extracts were incubated with prion peptide $PrP^{106-126}$ coupled to CNBr 4B SEPHAROSE (beaded agarose with wet bead diameter of 45–165 micrometers) beads overnight, with agitation.

Following the incubation, all bound material (i.e., anything binding to the $PrP^{106-126}$ peptide), was subjected to SDS-PAGE. To carry this out, the bound materials were separated, using a 40% stacking gel, and a 7.5% resolving gel. Proteins were then transferred to nitrocellulose filters (0.45 um pore size), and were then stained, with 0.5% PONCEAU S (3-hydroxy-4-[2-sulfo-4-(4-sulfophenylazo) phenylazo]-2,7-naphthalenedisulfonic acid), to verify extent of transfer.

FIG. 2 presents these results. Lane A is from the negative clone, and lane B from the positive clone. The eluates, when compared, revealed that a band for a protein of about 55–65 kD from the positive clones, was not found at a high level with the negative clones. In order to confirm this result, a Western blot was then carried out, as described below.

EXAMPLE 4

Cells from the positive clone were treated, as in example 1, but were not labelled. Also as in Example 3, the unlabelled protein extract was incubated with the $PrP^{106-126}$ SEPHAROSE (beaded agarose) beads, and bound protein was then eluted and applied to filters, also as described. For the Western blots, the filters were blocked with 5% fat dry milk in PBS, and then incubated with either normal mouse serum, or the antiserum described supra, and then goat anti-mouse biotin conjugated antibody. This labelled antibody was added for 1 hour at room temperature. After extensive washing, the antibodies wee developed, using a well known ECL chemiluminescent system. The results are depicted in lanes C–D of FIG. 2, with lane C obtained using normal serum, and lane D the antiserum against anti-prion peptide described supra. The findings suggest that the antiserum against anti prion peptide recognizes the $PrP^{106-126}$ binding band.

EXAMPLE 5

The examples set forth supra include analysis of co-cultures of neurons and glial cells. The possibility of glial cell labelling could not be discounted, and thus, a protocol was developed to test this possibility.

Glial cells were grown, in culture, using standard methodologies. The cultured cells were then lysed, and extracts were used in Western blot analyses, using the antiserum described supra. The glial cells were completely negative, as compared to the results which are depicted in FIG. 1. One may infer from this that the target of the antiserum is a molecule on neurons, i.e., it is a nerve cell antigen.

The foregoing examples set forth a peptide complementary to a peptide found in PrP. The PrP peptide is known, and is known to be neurotoxic. The inventive peptide, set forth in SEQ ID NO: 1, has been used to develop antibodies which can be used to identify neurons, since the target of the antiserum is specifically nerve cells.

Also a part of the invention is an isolated, anti-PrP protein, also referred to as an isolated, PrP binding protein which comprises SEQ ID NO: 1 as part of its amino acid sequence, and which has a molecular weight of from about 55 kilodaltons to about 65 kilodaltons as determined by SDS-PAGE. The protein, given its ability to bind PrP, is useful diagnostically.

As noted, the isolated 55–65 kD protein may be used to determine PrP in a sample. The methodology involves contacting a sample with the 55–65 kD protein to form complexes therebetween, followed by detection of the thus formed complex. The 55–65 kD protein may be immobilized, on a bead, column glass tube wall, and so forth, but need not be. If not immobilized, when complexes form in solution, these can be determined by observing migration patterns on a gel, or by way of any of the standard methodologies known to the art. Also, the isolated protein may be labelled, such as with a chromophobe, a radiolabel such as $^{125}I$, an enzyme, or any of the other standard labels used for determining binding. Presence of PrP in a sample may indicate the presence or predisposition toward a prion associated disorder, such as those described supra.

As noted, the peptide of the invention may be used per se in diagnostic methods, or as an immunogen. In the latter case, it may be coupled to a carrier, such as keyhole limpet hemocyanin, bovine serum albumin, or any of the standard materials used to "haptenize" small peptides. The resulting complexes comprising SEQ ID NO: 1, or the peptide per se, may be formulated in immunogenic compositions, such as with an adjuvant. As noted, the antibodies, which are produced following immunization with the peptides, can be used to detect nerve cells carrying the anti-PrP protein.

Other aspects of the invention will be clear to the artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

---

We claim:

1. A purified protein which has a molecular weight of from about 55 kilodaltons to about 65 kilodaltons as determined by SDS-PAGE, comprises the amino acid sequence set forth in SEQ ID NO: 1, and which binds to prion protein.

2. Isolated peptide consisting of the amino acid sequence of SEQ ID NO: 1.

3. Immunogenic complex comprising the isolated peptide of claim 2 complexed to a carrier.

4. The immunogenic complex of claim 3, wherein said carrier is keyhole limpet hemocyanin.

5. Immunogenic composition comprising the isolated peptide of claim 2 and an adjuvant.

6. Immunogenic composition comprising the complex of claim 3 and an adjuvant.

7. A method for determining prion protein in a sample comprising contacting said sample with the isolated protein of claim 1 and determining formation of complexes between said isolated protein and said prion protein as a determination of prion protein in said sample.

8. A method for determining prion protein in a sample comprising contacting said sample with the isolated peptide of claim 2 and determining formation of complexes between said isolated peptide and said prion protein as determination of prion protein in said sample.

* * * * *

UNITED STATES PATENT AND TRADEMARK OFFICE
CERTIFICATE OF CORRECTION

PATENT NO. : 5,679,530
DATED : October 21, 1997
INVENTOR(S) : Brentani et al.

It is certified that error appears in the above-identified patent and that said Letters Patent is hereby corrected as shown below:

In the cover page, line 15, under the section entitled Publications, insert "291" after "352:"

In the cover page, line 18, under the section entitled Publications, insert "291" after "352:"

In column 2, line 20, change "from" to read as -- form --.
In column 2, line 36, change "λ-endorphin" to read as -- ϒ-endorphin --.
In column 2, line 40, change "λ-endorphin" to read as -- ϒ-endorphin --.
In column 5, line 3, change "wee" to read as -- were --.

Signed and Sealed this

Fifteenth Day of May, 2001

NICHOLAS P. GODICI

*Attest:*

*Attesting Officer*     *Acting Director of the United States Patent and Trademark Office*